(12) United States Patent
Treppo et al.

(10) Patent No.: US 6,735,468 B2
(45) Date of Patent: May 11, 2004

(54) ARTHROSCOPIC IMPEDANCE PROBE TO DETECT CARTILAGE DEGENERATION

(75) Inventors: Steven Treppo, Richmond Hill (CA); Alan J. Grodzinsky, Lexington, MA (US); Emerson Quan, San Francisco, CA (US); Eliot Frank, Cambridge, MA (US); David Bombard, San Francisco, CA (US); David Breslau, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 82 days.

(21) Appl. No.: 09/776,254

(22) Filed: Feb. 2, 2001

(65) Prior Publication Data

US 2002/0045838 A1 Apr. 18, 2002

Related U.S. Application Data

(60) Provisional application No. 60/179,820, filed on Feb. 2, 2000.

(51) Int. Cl.$^7$ ................................................ A61B 5/05
(52) U.S. Cl. ...................................... 600/547; 600/587
(58) Field of Search ............................... 600/547, 587, 600/552, 439, 300, 383, 366; 607/5–8, 28, 63; 604/114; 606/41; 700/279; 762/158; 709/323, 108, 328

(56) References Cited

U.S. PATENT DOCUMENTS 5,246,013 A    9/1993  Frank et al.
5,779,651 A  *  7/1998  Buschmann et al. ........ 600/587

FOREIGN PATENT DOCUMENTS

WO    WO 92/06634    4/1992
WO    WO 96/08198    3/1996

OTHER PUBLICATIONS

Jeffrey R. Sachs et al., "An Electromechanically Coupled Poroelastic Medium Driven by an Applied Electric Current: Surface Detection of Bulk Material Properties," *PCH Physico–Chemical Hydrodynamics*, vol. 11, No. 4, pp. 585–614, 1989.

J. N. Van Der Molen et al., "Current Clamping Amplifier," *Medical & Biological Engineering & Computing*, vol. 17, No. 3, pp. 407–409, 1979.

* cited by examiner

*Primary Examiner*—Quang T. Van
(74) *Attorney, Agent, or Firm*—Gauthier & Connors LLP

(57) ABSTRACT

The change in tissue impedance due to the change in the extracellular matrix that results from the degradation of cartilage is utilized to detect degradation of articular cartilage. A probe applies a current to the articular cartilage which results in a current distribution and electric field within the cartilage, along with an associated voltage drop across the electrodes. The amplitude of this voltage drop is then measured and divided by the current applied to determine the tissue impedance. By measuring the impedance of patient tissue and comparing the detected patient impedance to a normal value for the tissue from clinically normal tissue, a determination of whether the patient tissue is degraded and the extent of degradation is possible. Preferably, the impedance is measured using a probe with interdigitated electrodes. By changing which electrodes are utilized, the wavelength of the current distribution changes, allowing the probe to image depth dependent focal lesions.

9 Claims, 6 Drawing Sheets

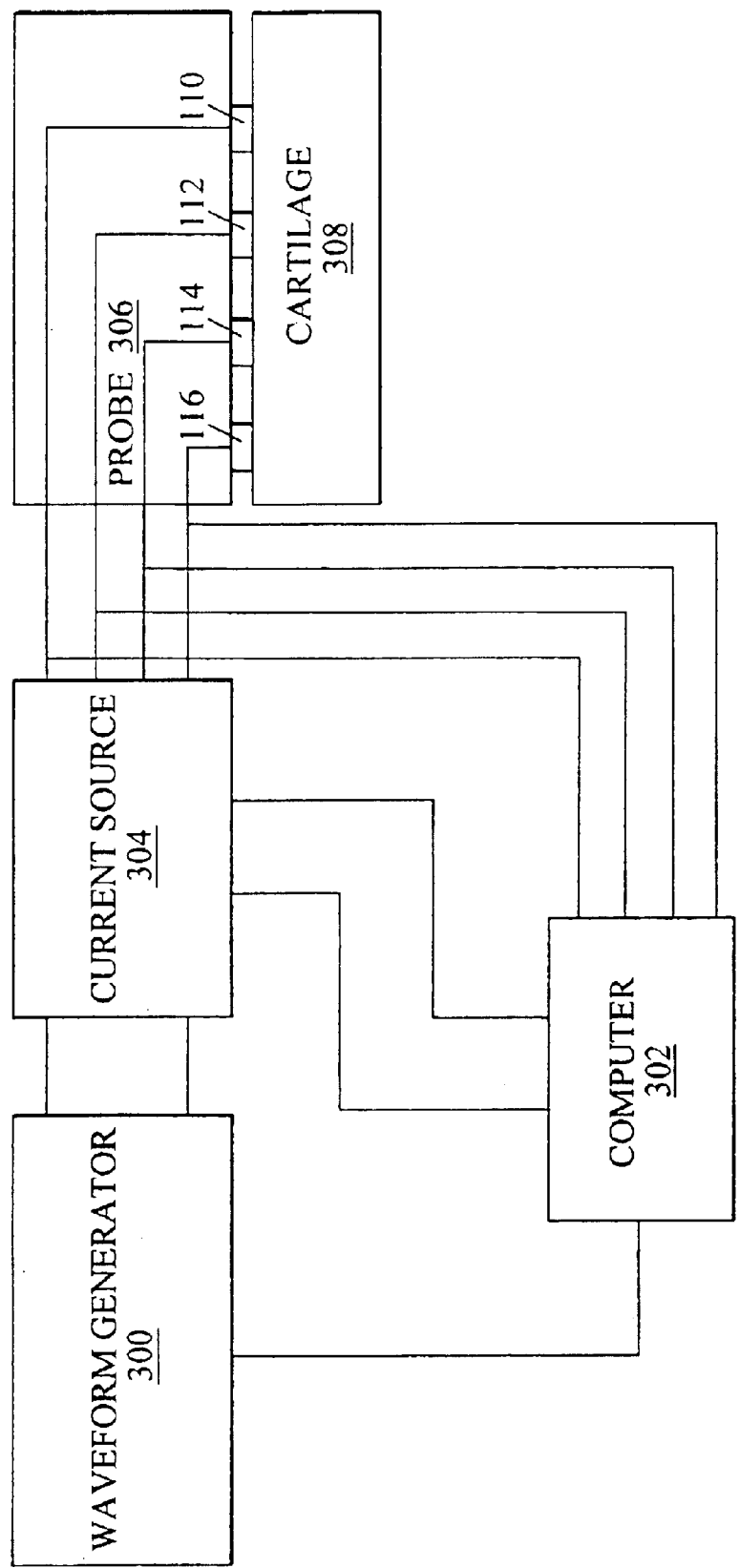

ARTHROSCOPIC IMPEDANCE PROBE TO DETECT CARTILAGE DEGENERATION

PRIORITY INFORMATION

This application claims priority from provisional application Ser. No. 60/179,820 filed Feb. 2, 2000.

This invention was made with government support under Grant No. AR 42285 awarded by the National Institutes of Health. The government has certain rights in the invention.

BACKGROUND OF THE INVENTION

The invention relates to the field of non-destructive arthroscopic diagnostic probes, and in particular to non-destructive arthroscopic diagnostic probes for detecting degeneration of articular cartilage utilizing impedance measurements.

Articular Cartilage

The function of organs in the human body are a direct consequence of their inherent structure. The function of an organ as a whole is more than the sum total of its individual constituents. Articular cartilage (AC) is a rich and illustrative example. An understanding of the composition and physical properties of AC are essential to diagnose a disease with any given device to aid in patient care. AC is a dynamic, living tissue that responds to stimuli in its environment (i.e. external loading, fluid flow, electric fields), and the cells of cartilage (chondrocytes) are able to maintain its intricate extracellular matrix (ECM). The scientific data collected over the past 25 years for normal cartilage, supports a hypothesis that a feedback between mechanical stimulation and chondrocytes must exist to maintain cartilage homeostasis.

By gross visualization, during knee arthroscopy or an open joint procedure, normal AC appears as a homogeneous shiny white substance covering the ends of articulating bones. It is a thin layer from 1 mm to 6 mm depending on the joint and particular surface location. In the presence of synovial fluid, AC provides a very low friction surface that has a coefficient of friction that is less than that of ice on ice. A closer inspection at the light microscopic level reveals AC as a very complex ECM of macromolecules with chondrocytes embedded within. Cartilage is a unique organ as it is aneural, alymphatic and avascular. Nutrient exchange to the chondrocytes proceeds by diffusion from synovial fluid at the articular surface and from the subchondral bone below. The lack of a blood supply severely limits AC's ability to be repaired following injury. The absence of innervation means that pain is transduced from the surrounding bone through unshielded force, or from the joint capsule in response to an inflammatory stimuli response.

The complex structure of AC acts as a loadbearing, shock absorbing, and wear resistant material to protect joint surfaces. In addition to a low friction surface, AC has a high compressive strength critical to pain free joint function. Compressive loads are distributed over a larger area, while also acting as a damping element during high impact loading (i.e. jumping). Cartilage is also strong in tensile loading when subject to shear stresses due to the sliding nature of joint function (i.e. knee joint or intervertebral disk). Lubrication by the synovial fluid also reduces shear stresses and helps protect the cartilage from trauma. These macroscopic mechanical properties are a direct consequence of the composition.

Articular cartilage is mostly water (60–80% of total weight) and ECM that comprises the bulk of the dry weight. The primary structural components of articular cartilage (AC) ECM are produced and maintained by the chondrocytes enmeshed within it. Tissue mechanical properties depend on the organization and structure of macromolecules present in the ECM. The ECM is made up of mainly collagen type II fibrils (along with small amounts of types IX and XI collagen), charged proteoglycans (PGs), and cells. Collagen and PGs form the framework for cartilage that resists applied mechanical forces. The collagen forms a dense cross linked network with PGs embedded within. Proteoglycans are macromolecules that contain polyanionic sulfated glycosaminoglycan (sGAG) chains. The negative fixed charge density of sGAGs is approximately 5.3 mEq/gm dry weight in normal human femoral head cartilage. A slight excess of mobile positive ions within the tissue preserves electroneutrality. At the macroscopic level a Donnan osmotic swelling force develops, caused by the electrostatic charge repulsion between the fixed anionic groups that draws water into the ECM, expanding the collagen network.

The chondrocytes are responsible for PG turnover (synthesis and degradation). The most abundant PG is aggrecan, which has an extended protein core with up to 150 chondroitin sulfate and keratan sulfate chains attached in a "bottle brush" structure providing a high concentration of anions. When first synthesized, aggrecan is mobile, but quickly binds to immobile hyaluranon, stabilized by a link protein, creating the high density of fixed $COO^{31}$ and $SO_3^-$ groups at physiologic pH.

Many other soluble factors play an important role in the maintenance process by participating as mediators of turnover and production of ECM, including ions, growth factors, hormones, cytokines, proteinases (e.g. matrix metalloproteinases) and their inhibitors. Numerous factors are required to maintain homeostasis. They can be produced by the chondrocytes themselves or synthesized elsewhere and transported into the ECM. These factors affect the chondrocytes through cell surface receptors and their transport through the ECM can be prohibited, resulting in pathology.

At the ends of articulating joints, the AC is 3–4 mm thick, with areas on the patella as high as 6–8 mm. Microscopically mature AC has 3 zones based on the shape of the chondrocytes and distribution of the type II collagen. The tangential layer has flat chondrocytes, tangential collagen fibril orientation and a sparse PG content. The intermediate layer is the thickest, with round chondrocytes, oriented in vertical columns. Finally, the basal layer has round chondrocytes and contains the tidemark that separates the uncalcified (nourished by the synovial fluid) and calcified cartilage (that gets fed by the episphyseal vessels). It has been reported that no age changes after maturation are discernible based on histology, including no loss of AC.

Collagen makes up the majority of the dry weight (approximately 50%) of AC, as it is also the most common structural protein in the body. In cartilage the most abundant form of collagen (>90%) is type II that acts as the structural meshwork of the ECM with its associated extensive intermolecular crosslinking via trivalent hydroxylysyl pyridinoline residues. The name "collagen" is a generic term for structural molecules that are rich in glycine, proline and hydroxyproline. Striated fibrils, type I, II, and III have three polypeptide chains wound in a triple helical configuration.

Type II collagen is composed of three left handed tightly interwoven alpha chains ($\alpha(II)_1$), 300 nm long and 1.5 nm in diameter., each with a repeating amino acid sequence of GlyPro(Hydroxyproline). It is the triple helical structure that enables collagen type II to have a high tensile strength. Hydroxylysine (some as hydroxylysyl pyridinoline crosslinks) helps type II collagen link together the ECM network.

Small amounts of collagen type IX help connect the various matrix elements together while type XI (approximately 3%) regulates the caliber of the fiber. In addition, collagen types VI and X are also present (<1%). Collagen type VI has a cross linking behavior and an increased amount has been reported in OA models, while collagen type X is associated with growth plate cartilage in the hypertrophic zone, and in the calcified layer of mature cartilage.

Individual aggrecan monomers are attached to a GAG core (hyaluronate), stabilized by link protein, with the number depending on the functional nature of the cartilage. The common PGs that can be found in cartilage include aggrecan, decorin, fibromodulin, and biglycan and make up about 35% of dry weight of AC. Aggrecan molecules form large aggregates (approximately 200 MDa) in cartilage, forming a hydrogel-like structure that is, in turn, immersed within the collagen type II fibers.

Aggrecan is the major PG in AC (around 90%) and is composed of two types of sulfated GAG (sGAG): chondroitin-6-sulfate, chondroitin-4-sulfate (approximately 20,000 MW) and keratan sulfate (approximately 5,000 MW). The amount of sGAG attached to each PG varies depending on the functionality and integrity of the tissue. Chondroitin sulfate GAGs are chains of repeating disaccharide units that contain highly charged carboxylate and sulfate groups. The high density of negatively fixed charge groups helps attract positive ions and create an osmotic swelling pressure to imbibe water within the tissue. There are approximately 100–150 sGAG chains per aggrecan molecule, while extremely large aggregates can bind thousands of GAG chains.

At the molecular level, the main unit of the aggrecan molecule is a protein core of approximately 300,000 MW. It has 3 associated globular domains: G1 and G2 at the N-terminus, and G3 at the C-terminus. The GAGs are mostly contained within the G2 to G3 domain. Keratan sulfate chains bind, in general, closer to the G1–G2 region (interglobular domain). The aggrecan PG varies in total size due to the varying amount of bound chondroitin sulfate. Therefore, proteoglycan is a combination of 5% protein and 95% carbohydrate.

Variation in the concentration of PGs has been observed with depth from the articular surface in immature and mature tissue, as well as location within a joint. Areas bearing higher stresses have also been shown to have a higher PG content. The charge groups on the GAG chains are ionized at physiologic pH providing a large osmotic swelling pressure that largely determines the equilibrium compressive modulus.

The main function of chondrocytes involves replenishment of macromolecular ECM constituents for its preservation in its harsh mechanical environment. With respect to the volume of the cartilage, the chondrocytes account for less than 5% and have a density of approximately $20 \times 10^3$ cells/mm$^3$. In fully developed tissue the size, shape and density of the chondrocytes vary with depth proceeding down from the articular surface. In general, the size increases, the shape moves from flat and elongated to spherical, and the density of cells decreases with increasing depth toward the underlying subchondral bone.

In order to perform their biosynthetic functions, chondrocytes are well equipped with an extensive endoplasmic reticulum and Golgi apparatus as well as mitochondria and secretory vacuoles. Chondrocytes are also involved in regulation of ECM assembly and repair by secreting and mediating their assembly. Because of its ability to produce degradating enzymes as well as their inhibitors, the chondrocytes are believed to participate in the physiologic as well as in the pathologic degradation of ECM.

Chondrocytes have also been shown to be able to adapt to the changes by biosynthetically responding to chemical, physical, mechanical and electrical stimuli through their cell receptors. These adaptations, through balancing the homeostasis of the ECM, alter integrity to conform with the stimuli. Biomechanical stimuli of cartilage explants (static or small amplitude dynamic compression) have been found to influence the rate of aggrecan synthesis and catabolism. This behavior may be due to changes in cell shape, specific cell-matrix interactions or change the availability of growth factors.

Investigators are also now beginning to look past the cell membrane to examine the intracellular changes due to mechanical compression on MRNA levels and also how cell deformation affects intracellular organelles like Golgi apparatus or endoplasmic reticulum to fulfill their functions.

Water is the most abundant component in AC, and it appears to be compartmentalized. Water that exists in the interstices of collagen molecules and fibrils is intrafibrillar water with the balance in the extrafibrillar space. The distribution between these two compartments has been reported to be a function of the fixed charge density and loading configuration of the tissue.

The total amount of water present is dependent on the interaction between the collagen and sGAG components, as the collagen fibril reinforcements in the tissue prevent full expansion by the sGAGs (due to their fixed charge density) and thus constrain water intake. This balance is perturbed in OA cartilage. An increase in water content is observed compared to healthy cartilage, despite an observable reduction in GAG content. The explanation of this contradiction lies in the assumption that damage to the collagen network severely impairs its ability to restrain the sGAG swelling pressure (despite its lower concentration in the tissue), thus the amount of water increases. One of the hallmarks of pathologic cartilage is its increased water content.

Matrix metalloproteinases (MMP) are an important group of zinc containing enzymes responsible for the breakdown of ECM components such as collagen and PGs in normal embryogenesis and remodeling as well as in many disease processes like cancer, osteoporosis and arthritis. These enzymes are almost universally distributed among mesenchymal cells of all types, and in some epithelial and endothelial cells as well. The family of MMPs can be divided into 3 subclasses: collagenases (MMP-1, MMP-8, and MMP-13), gelatinases (MMP-2 and MMP-9), and stromelysins.

The collagenases MMP-1 and MMP-13 are members of the family of matrix metalloproteinases that play an important role in the degradation and turnover of the ECM molecules such as type II collagen and aggrecan during normal remodeling (e.g. embryogenesis) and disease processing. MMP-1 and MMP-13 have been implicated in the progression of osteoarthritis and rheumatoid arthritis since they are found in the associated tissues at higher levels than in normal human tissue. The active enzyme has also been found at the lesion sites on the tibial plateaus of Hartley guinea pigs during the progression of spontaneous osteoarthritis. MMP-1 cleaves the three chains of the type II collagen molecule at specific sites, producing helical trimeric fragments of ¾ (from the N-terminus) and ¼ in length that can be detected using neoepitope antibodies. MMP-13 initially cleaves type II collagen at this same site, but can additionally cause a second cleavage, residues carboxy terminal to the primary cleavage site, and then a third cleavage site another three residues carboxy terminal to the second cleavage site. The time course of damage induced by MMP-13 is more rapid and transient than that due to MMP-1; MMP-13 was also found to turn over type II collagen 10 times faster than MMP-1 in humans.

It has been recently demonstrated through immunostaining of neoepitopes in cartilage from patients with osteoarthritis that type II collagen degradation was initiated by MMP-1 and MMP-13 at the articular surface and then extended into the middle and deep zones. In addition to this depth dependence, a direct correlation between the Mankin score of OA cartilage degradation and the intensity of the immunostaining of MMPs was recently found.

Electromechanical Effects of Articular Cartilage

As a consequence of the composition of cartilage, measurable electromechanical properties are exhibited (an area of research referred to as cartilage electromechanics). To consider modeling and analysis of AC behavior, AC can be conceptualized as a composite material of a fibrous mesh (collagen) embedded in a highly hydrated charged gel of PGs. Resistance to tension and shear loading is provided by the collagen, whereas the high swelling pressure of the PGs enables cartilage to resist compressive loading. The engineering properties of cartilage, i.e. compressive and tensile strength, have been assessed in many different systems. Extraction of PGs has produced a marked decrease in the tissue's equilibrium compressive modulus without effects to the tensile stiffness, while selective degradation of the collagen network predominantly affects tensile properties of the tissue.

The dynamic behavior of cartilage is the result of interactions between the solid ECM components and the interstitial fluid. Cartilage is most successfully modeled as a poroelastic medium. Such a medium is a fluid saturated porous material in which viscous effects are predominantly due to frictional interactions between the fluid and solid phases. The literature documents a rich history of mathematical models to describe this physical behavior of cartilage. Early work was begun by Biot almost fifty years ago in the context of geophysics. Using a mixture theory, where material properties and constitutive relations are derived separately for the fluid and solid phases, a biphasic theory describing the behavior of cartilage was developed by Mow and coworkers. These models of fluid flow can be related to mechanical properties like stiffness. Interest today remains high, with continued efforts to produce more complex nonlinear models for use with today's powerful computational capacity to more realistically model high strain behavior and the effects of nonhomogeneous material properties on experimental measurements.

Besides having mechanical properties, cartilage exhibits electrical properties that are coupled with mechanical stresses. It has been previously shown that these electrical interactions play a significant role in cartilage physiology.

The electromechanical transduction effect is a property of the cartilage composition, specifically the PGs and two dual phenomena are observed.

The first of these effects is known as streaming potential. As the hydrated ECM of cartilage is mechanically deformed, a flow of interstitial fluid relative to the fixed charge groups of the solid matrix is created. Entrained positive ions are separated from the negatively charged matrix macromolecules, giving rise to a voltage gradient or streaming potential in the direction of fluid flow. The second of these effects is the converse electrokinetic effect, known as current generated stress. This effect results when application of current causes an electrophoretic motion of the negatively charged fixed ECM molecules (PGs) towards the positive electrode and an electroosmotic motion of the mobile ions of the fluid phase towards the negative electrode. These combined effects produce a measurable bulk mechanical stress at the tissue surface that can be detected by an overlying stress sensor.

Osteoarthritis

Osteoarthritis (OA) is the most common disease that directly affects the everyday mobility and quality of life. It mainly strikes in the last quarter of life, but also occurs in young people after traumatic sports injuries. It attacks the tissue of the synovial joints (e.g., knees, hips, and hands) and is characterized by pain and accompanied by limitations in joint motion. It can progress to endstage, when patients can no longer walk pain free. Although the disease itself is not a significant source of mortality, it is a great cause of physical suffering. In the US alone, estimates that the number of people suffering from OA will reach 68 million by the year 2010.

Osteoarthritis describes a group of joint disorders that lead to the destabilization of normal AC function. Degradation and synthesis by chondrocytes of ECM are uncoupled. The initiation of OA may be a result of a variety of factors, including genetic, metabolic, developmental, and traumatic. OA is diagnosed clinically with sharp stabbing joint pain, tenderness, and inflammation leading to limitations of joint movement.

One of the early events in OA at a molecular level is alteration of the cartilage ECM, and the loss of the highly charged macromolecules (PGs) from the matrix. These changes often occur in localized regions of cartilage along the joint surface and to nonuniform depth. Investigators have hypothesized that such molecular changes should change the tissue's material properties.

Traumatic injuries can cause focal defects in cartilage adjacent to otherwise normal cartilage. Clinical repair approaches include debridement, microfracture, osteochondral plug resurfacing, and chondrocyte transplantation. During surgical procedures, and the subsequent follow-up, surgeons need to assess the state and functionality of the repair tissue. Often remodeling leads to a fibrocartilage repair tissue that appears cartilage like but has poor physical properties that ultimately lead to its failure.

In addition, there is a great need for methods to assess the efficacy of therapeutic interventions developed to prevent cartilage destruction or the patency of cartilage repair tissue. Presently, the assessment of cartilage repair is based on gross and microscopic morphological features. Detailed studies have established that the repair tissue is generally of good quality in the short term, but fails with time. At present, this behavior is difficult to explain. The literature shows only a minimal molecular characterization of the types of the cartilage repair tissue. The more that is understand of the repair process, the higher the chance to produce the optimal outcome; a repair tissue integrated in the native cartilage and biomechanically functional for many years. There is also a need for better in vivo, non-destructive diagnostic tools for quantitatively assessing degenerative changes in articular cartilage and to diagnose OA.

Diagnosis and Monitoring of Osteoarthritis

Current diagnostic criteria and methods for monitoring OA are based on external physical examination and x-rays. Efforts are being made to diagnose the disease progression at its earliest stages in order to apply treatment before further damage can occur. Initial diagnosis of OA begins with patients complaining of pain and stiffness in their joints. Further diagnosis can be made using the current gold standard of x-ray radiography. A grading scheme to characterize the damage is utilized; the most commonly used scale of radiographic evidence is the Kellgran and Lawrence method. The scale is numbered from 0 to 4 with 0 being no visible defects and 4 showing visible OA.

Radiographic diagnostic criteria has three main shortcomings: they lack sensitivity, the emphasis is on changes to the bone, and reading the films is subjective with poor reproducibility. Studies have shown that after 2 years of treatment with NSAIDS, the radiographs showed no significant changes. It is possible that the sensitivity is simply too low to detect small treatment effects. The limitations of radiographs include: nonstandard and shifting of joint positions, the x-ray beam alignment, radiographic magnification not taken into account and landmarks for measurement can be subject to individual interpretation. These defects have been corrected in current clinical trials. However, x-rays cannot visualize cartilage. They measure the space between bony surfaces that could be filled with cartilage and thus, are an indirect measure of the absence of cartilage or a failure of compressive resistance of existing cartilage. Thus, x-rays only examine cartilage status and can reveal bone and then joint involvement only in the later stages of disease.

Laboratory methods such as a synovial fluid extraction or a histological examination (Mankin scale) can be used to further investigate the progression of disease. Unfortunately, synovial fluid extraction can only rule out other possible causes for the pain, such as rheumatoid arthritis. The Mankin scale categorizes the extent of disease progression in tissue via histology but requires a destructive biopsy. Furthermore, histological examination occurs only where tissue was removed.

Other possible methods include MRI, sonography, scintography, and biochemical markers, but they too have limitations in detecting changes in cartilage. MRI concentrates on biochemical composition studies that could yield measures of the sGAG and collagen concentrations, but at this stage the cost is very high and the fixed charge density too low for adequate resolution. As such, clinical MRI approaches do not have the resolution to show early cartilage changes and do not measure physical properties.

Arthroscopy has become an important technique in the diagnosis and therapy of knee OA. A 4 mm diameter arthroscope and/or surgical instruments along with a light source is inserted into the joint capsule, allowing direct visualization of the cartilage surfaces, ligaments, and menisci. The complication rate and morbidity associated with the procedure are so low, that arthroscopy is increasingly being performed on joints that are only minimally symptomatic as an exploratory procedure. It can detect before degenerative changes are evident by radiography. The recent advent of a 1.8 mm diameter needle arthroscope is transforming arthroscopic examination from a hospital-based procedure to a routine office procedure. During a typical diagnostic arthroscopic examination of the knee, the orthopedic surgeon can inspect the AC surface for gross changes. Arthroscopy is performed visually without quantitative biophysical methods. Ultimately, these gross visualization arthroscopic methods, give a visual picture of the cartilage that may or may not correlate with its physical properties.

It is important to note that early OA cartilage may appear normal by visual inspection. Given that arthroscopy is one of the most common orthopedic procedures, visual inspection alone during arthroscopy may not be sufficient for diagnostic purposes, indicating a need for quantitative approaches.

There is currently a commercial arthroscopy blunt probe to subjectively assess the degree of softening (known as "grade I chondromalacia") that can result prior to x-ray changes. Another device and method to measure the physical properties of articular cartilage has been developed by Dashefsky (*Arthroscopy*, 3:80–85, 1987). Dashefsky designed a more objective measurement apparatus. He used an instrumented indenter attached to a force transducer to qualitatively assess the mechanical properties of chondromalacia of patellar cartilage during arthroscopy. In a group of 107 knees with "patellofemoral symptoms and signs", 90% were evaluated as "soft;" but over half of these "soft" cartilages showed no detectable visual changes of the articular surface of the patella. Interestingly, of 58 patients with no signs or symptoms of the patella, 50% showed softening of the cartilage. These results suggest that physical property changes may not correlate with the patients' symptoms until an irreversible threshold of damage occurs with the chronic wear and tear of cartilage.

More recently, Lyyra et al. (*Med. Eng. Phys.*, 17:395–399, 1995), developed an arthroscopic indenter instrument with strain gauges for measurement of tissue stiffness in vivo, produced as Artscan 1000 from Artscan Medical Innovations, Helsinki, Finland. A constant deformation is imposed on the cartilage by the indenter, and the "instantaneous" load response during a one second measurement interval is used to evaluate the tissue stiffness before appreciable stress relaxation has occurred. In order to compute an effective dynamic modulus, an independent measurement of tissue thickness is necessary, as with any indentation technique. The device was able to detect differences in the stiffness of cartilage in different regions of normal knees. Interestingly, however, the indenter detected only 30–40% decreases in cartilage stiffness in the most severely affected regions of the patellar cartilage of patients with known chondromalacia. Use of these devices indicates that purely mechanical tests alone (e.g., indentation tests) may not provide a sufficiently sensitive index of early degenerative changes in cartilage. Because of this, the cartilage's electromechanical transduction properties have been incorporated into a surface diagnostic probe.

This approach has been termed electromechanical surface spectroscopy and utilizes the current generated stress phenomena of articular cartilage. Spatial and temporal changes in the molecular integrity of the collagen network due to degeneration lead to important changes in the functional mechanical and electrical properties of the tissue and therefore cause changes in the current generated stress. In this approach, illustrated in FIG. 1, small sinusoidal electrical currents are imposed by an interdigitated electrode array 104 that rests on the cartilage articular surface 100. The current causes an electrophoretic motion of the negatively charged cartilage extracellular matrix (ECM) towards the positive electrode and an electroosmotic motion of intratissue fluid towards the negative electrode. These combined effects produce measurable normal mechanical stresses at the tissue surface that can be detected by an overlying piezoelectric stress sensor 102. The stress produced is at the same fundamental frequency as the driving current, but out of phase due to the poroelastic nature of the cartilage response. The penetration depth into the tissue is proportional to the spatial wavelength of interdigitated electrode 104 structure, defined as twice the electrode spacing.

This electromechanical technique is generally described in U.S. Pat. No. 5,246,013. In addition, for this technique, Frank et al. (*J. Biomech.*, 20:629–639, 1987) utilized a uniaxial configuration in which the current was applied via electrodes on opposite ends of a excised cartilage plug. Sachs et al. later completed a mathematical model showing that two silver electrodes placed on the same surface side of cartilage could induce a measurable mechanical response when current is applied in this potentially nondestructive arrangement (*Physiochem. Hydrodyn.*, 11:585–614, 1989 and *A Mathematical Model of an Electromechanically Coupled Poroelastic Medium*. PhD thesis, Massachusetts Institute of Technology.). In parallel, Salant et al. (*Surface Probe for Electrokinetic Detection of Cartilage Degeneration*. MD thesis, Harvard-MIT Division of Health Sciences and Technology.) and later Berkenblit et al. (*Spatial Localization of Cartilage Degradation Using Electromechanical Surface Spectroscopy With Variable Wavelength and Frequency*. PhD thesis, Massachusetts Institute of Technology.) improved on this design by designing a configuration in which current could be applied to a single surface of cartilage and the resultant induced mechanical stress could be measured.

The general technique has also been termed "imposed-k sensing" because the medium is excited at a specified temporal (angular) frequency, by an electrode structure having a spatial period=2/k determined by the electrode geometry and hence a dominant wave number k. Its advantages are that it can be made nondestructively (an important requirement for in vivo measurement of cartilage properties) and the electric fields generated decay exponentially into the material, with a penetration depth on the order of /5 to /3. Thus, different depths of the material may be tested by varying the imposed spatial wavelength, and spatial inhomogeneities in material properties can be detected by making surface measurements using a series of imposed spatial wavelengths (spatial localization). The depth to which the current penetrates into the medium is proportional to the effective spatial wavelength, which is equal to twice the center-to-center distance between adjacent electrodes. By changing the imposed spatial wavelength (by having independently addressable electrodes), various depths of the medium can be preferentially assessed.

The use of varying wavelengths is illustrated in FIGS. 2a and 2b, collectively. Both the frequency and wavelength of the applied current density affect the depth of penetration of the current induced poroelastic deformation within the tissue. The characteristic depth of penetration of the current density, itself, is approximately the spatial wavelength of the current. This wavelength, is determined by the electrode excitation pattern at the cartilage surface. Therefore, a probe with four independently addressable electrodes 104 is utilized such that connection to each electrode can be varied externally, thereby enabling multiple wavelengths to be applied using a single device. Applied current densities having short wavelength, illustrated in FIG. 2a, compared to cartilage thickness are confined to the superficial region of the tissue; the associated current generated stress will therefore reflect the properties of the superficial zone. In contrast, long wavelength excitations, illustrated in FIG. 2b, penetrate the full depth of the tissue and thereby reflect the average properties of full thickness cartilage. Thus, combinations of short and long wavelength excitations enable the probe to "image" depth dependent focal lesions.

Spectrometer 102 response depends in a sensitive manner on molecular level changes in the cartilage matrix similar to changes that occur during the earliest phases of OA degeneration. These results provide the fundamental basis for the in vivo surface electromechanical spectroscopic approach to detect cartilage degeneration.

For this method, typically a sinusoidal current density of 1 mA/cm$^2$ is applied to the tissue over the frequency range 0.025–1.0 Hz using a bipolar operational amplifier, such that the total current amplitude is constant at all frequencies, and driven by a programmable frequency generator controlled through a computer. The output of the piezoelectric sensor electrodes are passed through a high impedance electrometer, low pass filtered to remove 60 Hz noise and differentially amplified. The signals are recorded on a computer, and combined with a mechanical sensor calibration done before each test to obtain the current generated stress. By comparison of this current generated stress to the current generated stress in normal cartilage, a determination can be made as to whether the present cartilage has experienced degradation.

While electromechanical spectroscopy is useful in detecting cartilage degeneration, there is still an ongoing need for in vivo techniques to non-destructively and rapidly test for cartilage degeneration. Experiments have shown that use of the electromechanical spectroscopy may be not be able to sensitively measure surface cartilage damage, to a depth of approximately 50 $\mu$ms, caused by MMP-13. In addition, the most sensitive detection afforded by current generated stress techniques requires measurements at lower frequencies, which require longer measurement time. The present invention overcomes these disadvantages, in addition to providing further advantages when utilized alone, or in conjunction with electromechanical spectroscopy.

SUMMARY OF THE INVENTION

A probe for detecting the degeneration of mammalian tissue, particularly articular cartilage, which comprises a pair of electrodes for applying a current to the mammalian tissue is provided. When current is applied to the tissue there is a distribution of current density and an electric field within the tissue, and a resulting voltage difference across the electrodes applying the current. In the preferred embodiment, the voltage difference is measured by a computer, and the computer normalizes the voltage difference to the current applied to the tissue. This normalized parameter is defined as the tissue impedance. The impedance is indicative of the amount of degeneration tissue has undergone.

In an alternative embodiment, electrodes of the probe comprise an interdigitated array of electrodes allowing the wavelength, and hence, the depth of penetration of the current distribution into the tissue to be changed. When a short wavelength mode is utilized, the impedance measurements are representative of a superficial layer's degeneration. When a long wavelength mode is utilized, the impedance measurements are representative of the bulk tissue degeneration.

In an alternative embodiment, the probe additionally comprises a stress sensor. The current applied to the tissue creates current generated stress in the tissue. This stress is measured and additionally used to determine whether degeneration has occurred. In one embodiment, impedance measurements are taken simultaneously with the current generated stress measurements at the same frequency as the current generated stress measurements. In a different embodiment, the impedance measurements are taken sequentially, i.e. after the current generated stress measurements, at a frequency higher than those at which the current generated stress measurements are made.

A method for detecting the degeneration of mammalian tissue, particularly cartilage, is provided. Current is applied to the tissue creating a distribution of current density and an electric field within the tissue, and a resulting voltage difference across the electrodes applying the current. The amplitude of the voltage difference across the electrodes is measured and divided by the current applied by the electrodes to give the tissue impedance. This tissue impedance is compared to an impedance value of clinically normal tissue to determine if the tissue is degenerated.

In one embodiment, the voltage difference across the electrodes applying current is measured simultaneously to a current generated stress measurement and at the same frequency as the current generated stress measurement. In another embodiment, the voltage difference is measured at a higher frequency than that used for current generated stress measurements, either alone, or after current generated stress measurements have been made.

BRIEF DESCRIPTION OF THE DRAWINGS

FIG. 3 illustrates a system according to the present invention for measuring the impedance of cartilage to detect degradation of the cartilage.

DETAILED DESCRIPTION OF THE INVENTION

Operation of the Invention

Figure 1:
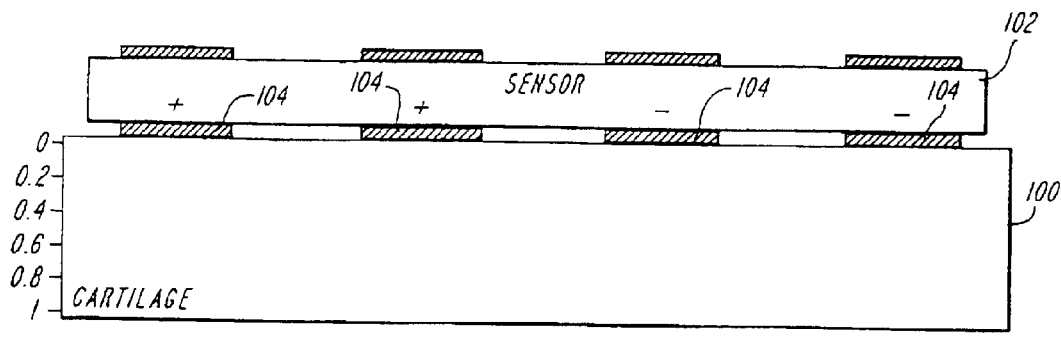
FIG. 1 illustrates the sensor and electrodes for current generated stress measurements.
Figure 2A:
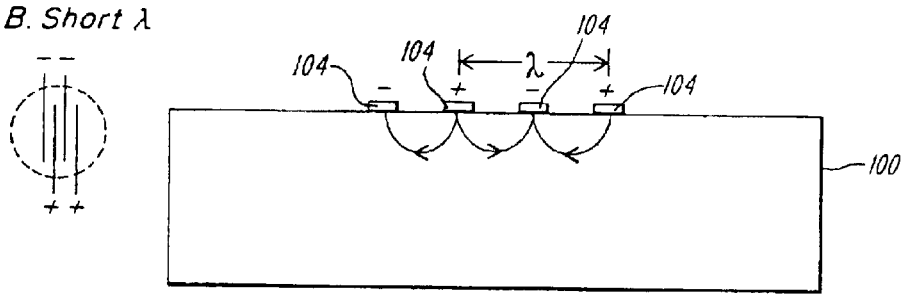
FIG. 2 illustrates the short and long wavelength modes for current generated stress measurements.
Figure 2B:
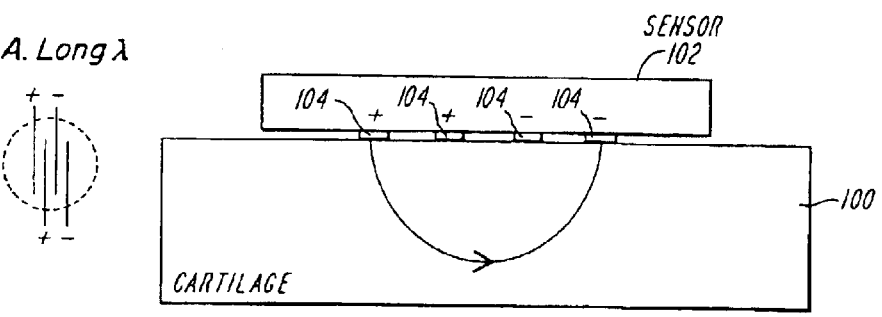

When current is applied to articular cartilage there is a distribution of current density and an electric field within the tissue, and also an associated voltage drop across the electrodes applying the current. The amplitude of the measured voltage drop between electrodes divided by the applied current amplitude is defined as the electrical impedance. The electrical impedance of the tissue for frequency ranges at least up to approximately 1 kHz, and possibly further, is dominated by the resistance of the hydrated ECM and this resistance is inversely proportional to the density of mobile ions within the intratissue fluid. Thus, the electrical impedance of the tissue will increase with decreasing PG fixed charge content or increased swelling at constant PG content, since both these conditions lead to a lower concentration of mobile ions in the ECM by Donnan equilibrium. In addition, collagen network degradation will alter impedance.

This change in impedance due to the change in the cellular matrix that results from the degradation of the cartilage is utilized to detect degradation of articular cartilage. By measuring the impedance of patient tissue and comparing the detected patient impedance to a normal value for the tissue from clinically normal tissue, a determination of whether the patient tissue is degraded and the extent of degradation is possible. Preferably, the impedance is measured using a probe with interdigitated electrodes similar to that used for electromechanical spectroscopy. In this manner, the probe is able to "image" depth dependent focal lesions.

The use of impedance to determine cartilage degradation provides for a number of advantages:

Higher frequencies (e.g. 1 kHz) than those used for electromechanical spectroscopy can be used, increasing the speed with which measurements are performed.

No need for complex signal processing.

For an impedance-only probe, there is no need for a mechanical calibration step and eliminates the difficulties of manufacturing probes with the sensitive behavior of a piezoelectric sensor.

When impedance is utilized with current generated stress (CGS, i.e. electromechanical spectroscopy) measurements (in the low frequency range, 0.25–1.0 Hz, where CGS is detectable), impedance is measured simply by monitoring the voltage across the probe inputs.

Electrodes for impedance measurements are able to be made arbitrarily small in any arrangement to control spatial sensitivity of the impedance measurements to possible diagnose cartilage abnormalities in small animals (e.g. rats) where the cartilage may only be 100 $\mu$ms thick.

Acquisition of data over a wider frequency range.

An increased precision of measurements resulting from smaller standard deviations.

FIG. 3 illustrates a system according to the present invention for measuring the impedance of cartilage to detect degradation of the cartilage. A waveform generator 300 applies a sinusoidal voltage waveform to a current source 304 such that the total current amplitude is constant at all frequencies. A computer 302 controls waveform generator 300. The current generated by current source 304 is applied to the electrodes 310, 312, 314 and 316. Preferably, multiple independently addressable electrodes are utilized so as to be able to generate both long wavelength and short wavelength excitations. As previously described, applied current densities having short wavelength compared to cartilage thickness are confined to the superficial region of the tissue. Therefore, the associated measured impedance reflects the properties of the superficial zone. In contrast, long wavelength excitations penetrate the full depth of the tissue and as such, the measured impedance associated with long wavelength excitations reflects the average properties of full thickness cartilage. Thus, combinations of short and long wavelength excitations enable the probe to "image" depth dependent focal lesions.

To measure the impedance, computer 302 measures the current applied to cartilage 108 through electrodes 310, 312, 314 and 316. In addition, computer 302 measures the voltage drop across the electrodes applying the current to cartilage 308. By normalizing the voltage drop to the current applied, the impedance of cartilage 308 is measured. The impedance is then compared to clinically normal tissue to determine whether degradation has occurred in the tested tissue. It should be noted that, while a computer is preferred to measure the voltage and determine the impedance, other equivalent devices such as a voltmeter, an application specific integrated circuit, or a chip internal to the probe can be utilized to either measure the voltage or determine the impedance without departing from the scope of the present invention.

Detecting cartilage degradation using impedance relies on detecting changes in tissue conductivity resulting from loss of aggrecan charge groups and/or degradation of the collagen network. However, even complete loss of GAG from the tissue would decrease the electrical conductivity by only about 28%, while electrokinetic coupling, and thus the current generated stress amplitude, would decrease to zero. Thus, as is the case with purely mechanical measurements of cartilage material properties, measures of purely electrical properties, such as impedance, may be a less sensitive indicator of degradative changes than measurement of electromechanical quantities such as current generated stress. Therefore, in the preferred embodiment, the impedance measurements are utilized in conjunction with the current generated stress measurements previously described. When measured in conjunction with the current generated stress measurements, impedance measurements are made in the low frequency range, 0.25–1.0 Hz, where current generated stress is detectable, simultaneously with the current generated stress measurement. However, the impedance measurements are able to be made alone, or following the current generated stress measurements. When the impedance measurements are made alone, or following the current generated stress measurements, rather than simultaneous with the current generated stress measurements, it is preferable to make the impedance measurements in a frequency range of approximately 1 kHz in order to allow the measurements to be taken rapidly, making it less sensitive to surgeon hand tremor. In addition, measurement of cartilage impedance over a range of frequencies could also provide additional information about the tissue, such as an estimate of cartilage thickness.

Figure 4:
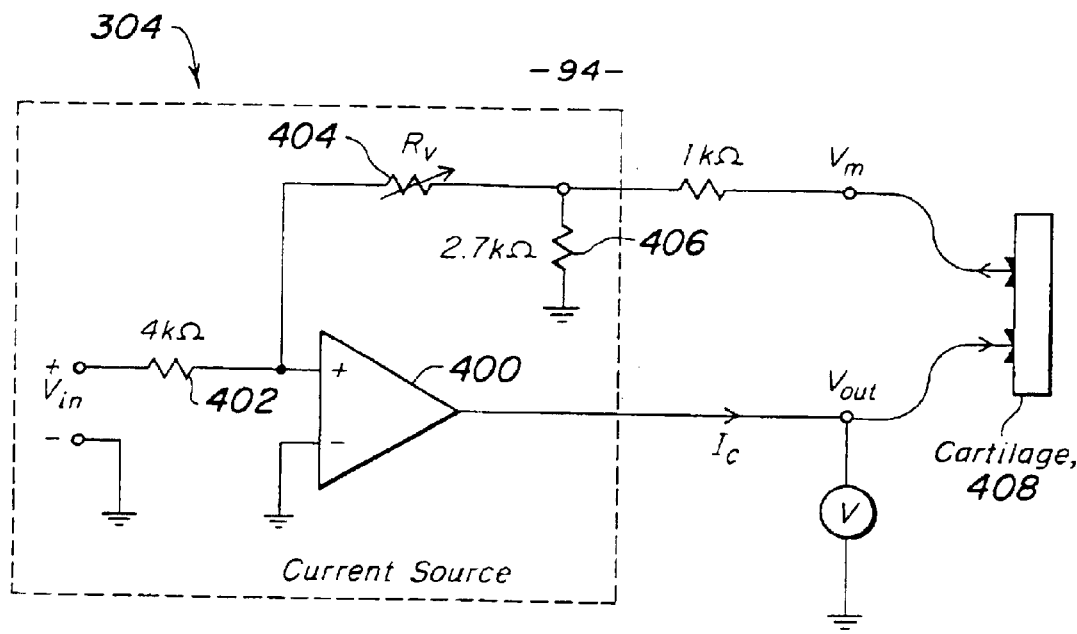
FIG. 4 shows a schematic of a preferred embodiment of the current source.

FIG. 4 shows a schematic of a preferred embodiment of current source 104 that delivers current to the probe at the cartilage surface. Current source 304 is depicted used with a two-electrode probe for simplicity.

Current source 304 comprises a bipolar operational amplifier 400, resistor 402, variable resistor 404 and resistor 406. When a sinusoidal input voltage ($V_{in}$) is provided to current source 304 from waveform generator 300, a resultant current $I_c$ to the cartilage is produced. The current applied to cartilage also results in a voltage difference $V_{out}$-$V_m$, between the electrodes on cartilage 408. This voltage difference is measured and divided by the current $I_c$ to obtain the measured impedance $Z_{meas}$.

Figure 5:
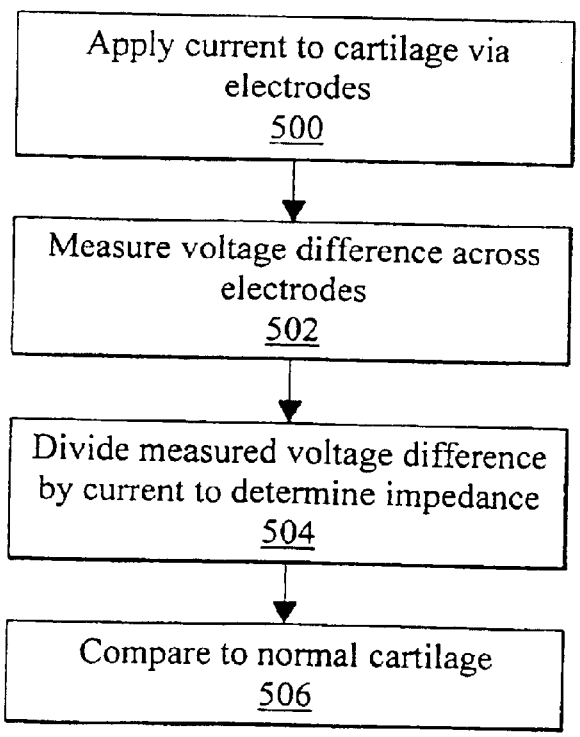
FIG. 5 illustrates the general method for determining whether cartilage degradation has occurred in test cartilage utilizing impedance measurements.

FIG. 5 illustrates the general technique for determining whether cartilage degradation has occurred in test cartilage utilizing impedance measurements. A sinusoidal current is applied to the electrodes on the surface of the cartilage by a current source 500. As the current is applied to the cartilage, the voltage difference present across the electrodes is measured 502 by a computer. The measured voltage difference is then divided by the current applied to the electrodes to obtain the impedance 504. This impedance is then compared to the impedance of clinically normal cartilage to determine if degradation is present 506.

Exemplary Embodiment of Arthroscopic Probe for Detecting Cartilage Degradation

Electrode/Transducer Structure and Fabrication

It should be noted, as the preferred embodiment of the present invention comprises impedance measurements utilized along with current generated stress measurements, the preferred embodiment of the electrodes and probe include a stress sensor and the following description will include the stress sensor as part of the electrodes and probe. However, the present invention should not be seen as limited thereto.

Figure 6A:
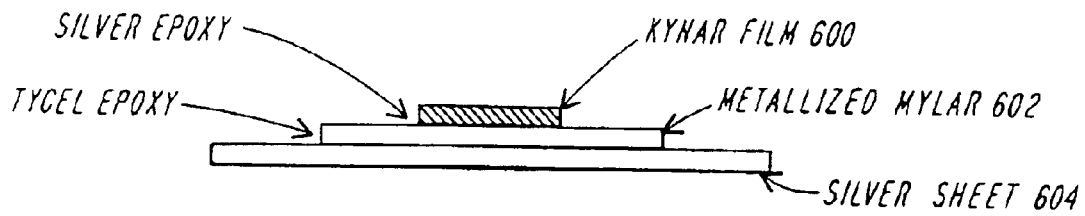
FIGS. 6a and 6b, collectively, illustrate the layers that comprise the electrode/transducer structure for the preferred embodiment of the probe.
Figure 6B:
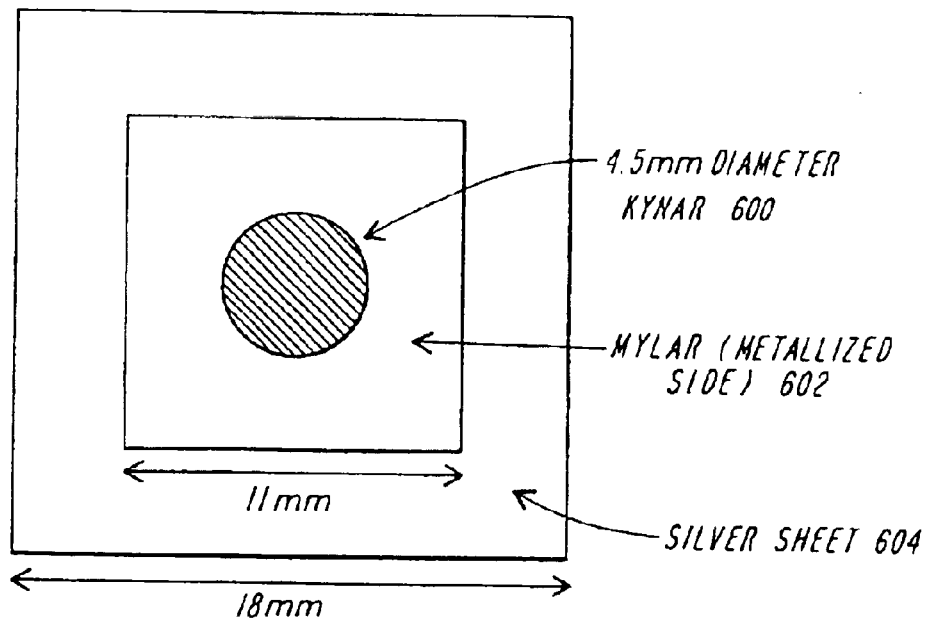

The electrode/transducer structure (ETS) is the working component of the "probe" system, applying current to the cartilage surface and measuring the resultant stress from a piezoelectric film. Preferably, it is a flexible, 180 µm thick, 3 layer laminated structure. FIGS. 6a and 6b, collectively, illustrate the layers it is comprised of:

Silver excitation electrodes are etched from a sheet of silver foil 604 and deposited with a layer of silver chloride in an appropriate electrochemical cell. Preferably, silver foil layer 604 for the excitation electrodes is made from a 25.4 µm thick silver foil cut to a size of 18×18 mm with a sharp straight edge. The use of Ag/AgCl electrodes decreases the low frequency impedance between the electrode and cartilage while stabilizing the electrode potential.

A shielding layer 602 is preferably made from 25.4 µm thick Mylar™ polyester film metallized (on one surface) with a thin layer of aluminum and is cut to 15×15 mm. Shielding layer 602 separates the silver electrodes and stress sensors while also serving as a ground/isolation plane. The metallization is a ground plane that helps shield the sensitive stress sensors from electromagnetic interference (principally electric fields emanating from the excitation electrodes) when the ETS is placed in the probe body.

The stress sensor is fabricated from a single sheet of 52 µm thick polyvinylidene fluoride (PVDF) with a thin (100 Å) sputtered nickel-copper alloy metallization on both sides 600, known as Kynar™, from AMP Inc., Norristown, Pa. Preferably, Kynar™ layer 600 is punched to a disk of 4.5 mm in diameter (the size of the "active" area of the probe). This piezoelectric material transduces the mechanical stress sensed to a measurable voltage signal. The metallization on one surface of the Kynar™ is etched to form electrodes that register with the silver electrodes on the opposite side of the ETS. The other side of the PVDF is connected to the ground/isolation layer 602. Kynar is preferable for the stress sensor in this application for a number of reasons:

it has a high sensitivity to mechanical stress especially in this low frequency (0.025–1.0 Hz) application, allowing the film to behave as a compact strain gauge with no external power source, the generated dynamic signals are greater than those from typical strain gauges after amplification, and the flexible sheets are relatively inexpensive and can be cut into arbitrary patterns.

To characterize the sensor as a stress gauge, a force applied normal (forces in the plane of the electrode are neglected) to the surface of the film develops an electric surface charge on the metallization proportional to the mechanical stress. The charge Q [coulombs] developed by a stress [N/m$^2$] over an area A [m$^2$] can be described by Q=d$_t$A, where d$_t$ is an empirically determined piezoelectric strain constant. The open circuit voltage between the metallization on either side of sheet 600 is the charge divided by the capacitance, A'/, where is the dielectric constant of the film and is the film thickness. If part of the total metallized area is not being loaded, it adds to the capacitance without generating any charge, thus decreasing the measured voltage. Representing the total area by A' and the active area being loaded by A, the equation for the open circuit voltage signal becomes:

$$V = Q/C_{total} = d_r A/A' = d_r A/A'$$

For maximum sensitivity, it is desirable to maximize the measured voltage signal, V, for a given stress, thus $A/A'\sim 1$. The voltage output also depends on film thickness. As electrodes are more tightly packed onto the ETS, a thinner film may be needed to gain sufficient spatial resolution with respect to electrode spacing.

The assembly procedure of fabricating this laminated structure is characterized in the following phases:

Phase I—ETS Construction

The sheets are rinsed with a mild detergent and then deionized water, while handling is done with disposable latex gloves to keep all materials clean to prevent contamination with oils and dirt. To aid in the photofabrication, both sides of the silver foil are gently abraded with a fine abrasive and then dipped in a 15% v/v nitric acid solution. To form a laminated structure, silver foil 604 is bonded to the non-metallized side of the shielding layer 602 using a two-part urethane epoxy in a 50:1 ratio (e.g. Tycel 7000/7200, Lord Corp., Erie, Pa.) thinned with methyl ethyl ketone. Silver foil 604 is larger to allow press fit connections with copper tabs in the periphery of the inner core when the probe is assembled. Sensor layer 600 is bonded to the metallized side of the shielding layer 602 with a manually applied thin film of silver conducting epoxy (e.g. TRA-DUCT 2902, TRA-CON Inc., Medford Mass). The ETS is pressed together for a few minutes to assure good bonding and is allowed to cure overnight.

Phase II—Photofabrication

To form the silver excitation and the piezoelectric stress sensor electrodes, standard photofabrication techniques are used. The surfaces are coated with a light sensitive organic polymer, photoresist, which becomes inert to the etching chemicals when cross linked by ultraviolet light. A negative of the electrode pattern desired is used to selectively cross link the photoresist, then etching chemicals are used to isolate the electrodes.

Figure 7A:
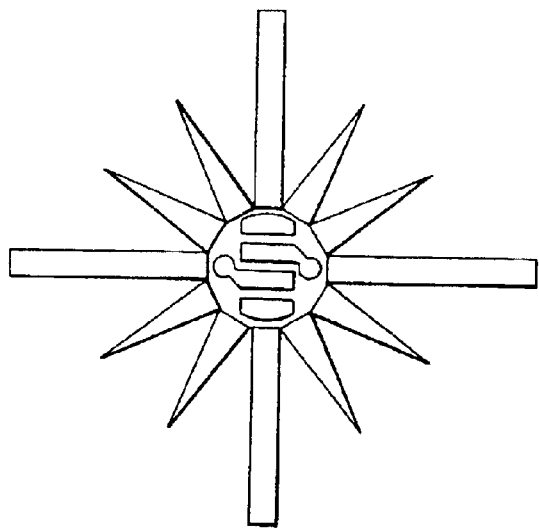
FIGS. 7a and 7b illustrate the electrode patterns for the excitation electrodes and sensor electrodes of the preferred embodiment of the probe.
Figure 7B:
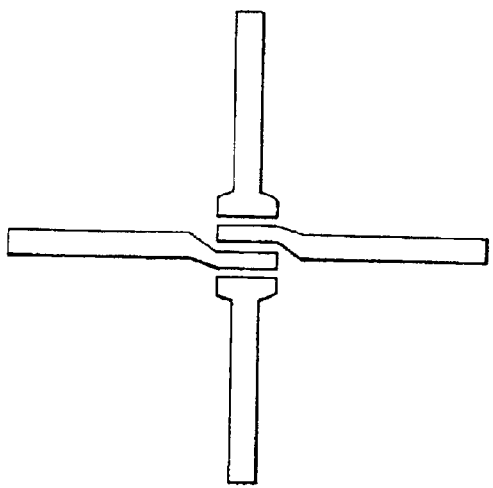

The ETS is dehydration baked at 80° C. for 10 minutes in a convection oven to remove residual moisture, and both sides are coated with a photoresist compound, hung to dry for 30 minutes in a darkroom, and then baked between paper and glass plates (to keep them flat) at 80° C. for another 10 minutes. Electrode patterns are converted to negative images (masks) on two photographic transparencies. A dry, photoresist coated ETS is placed between the two masks, aligned so the electrodes are registered on opposite sides of the ETS, then exposed to ultraviolet light for 15 minutes. The ETS is then bathed in a xylene-based developer solution for 30 seconds, transferred to another bath of developer for 30 seconds, and then rinsed under warm tap water and blotted dry. The developer removes the uncross linked photoresist, leaving the resist behind in the desired electrode pattern. The electrode pattern for the sensor electrodes on Kynar™ layer 600 is illustrated in FIG. 7a, while the excitation electrode pattern for silver layer 604 is illustrated in FIG. 7b.

Phase III—Etching

Etching of the silver metallization occurs while the ETS is mounted in a custom made two-part poly(methyl methacrylate) holder with a rubber O-ring gasket to contain the etchant. An appropriate etchant is a 55% w/v solution of ferric nitrate heated to 45° C., with the silver side of the ETS exposed to a fresh etchant bath every two minutes. The thin metallization on the piezo film is etched, by carefully placing a few drops of etchant on the surface, waiting only 5–10 seconds, and quickly rinsing with deionized water. The photoresist is finally removed from both sides with a cotton swab dipped in xylenes.

Figure 8:
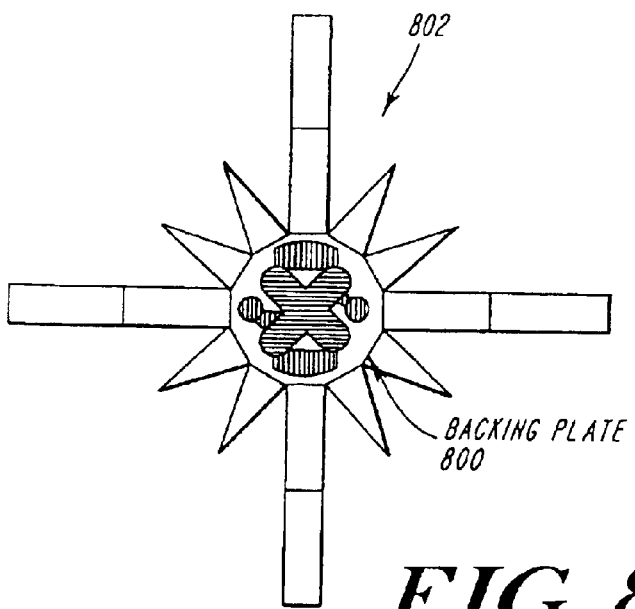
FIG. 8 illustrates the backing plate on the electrode/transducer structure of the preferred embodiment of the probe.
Figure 9D:
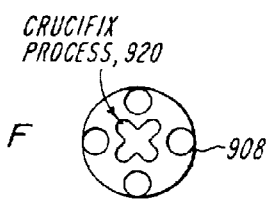
FIGS. 9a–9d, collectively, illustrate the probe structure for the preferred embodiment of the probe.
Figure 9C:
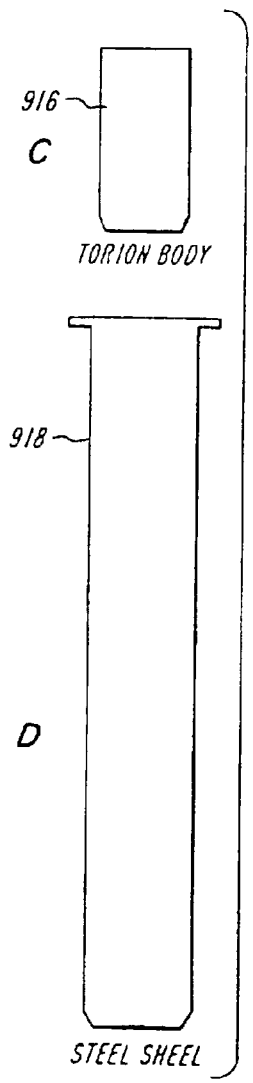
Figure 9B:
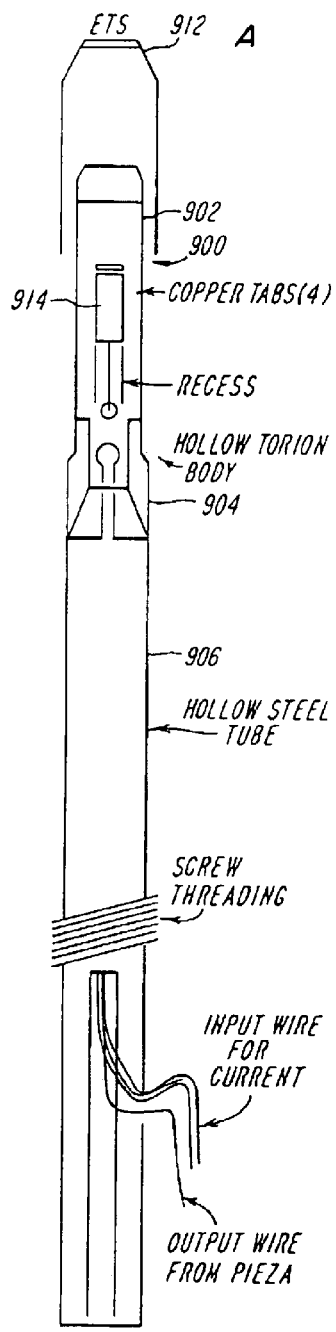
Figure 9A:
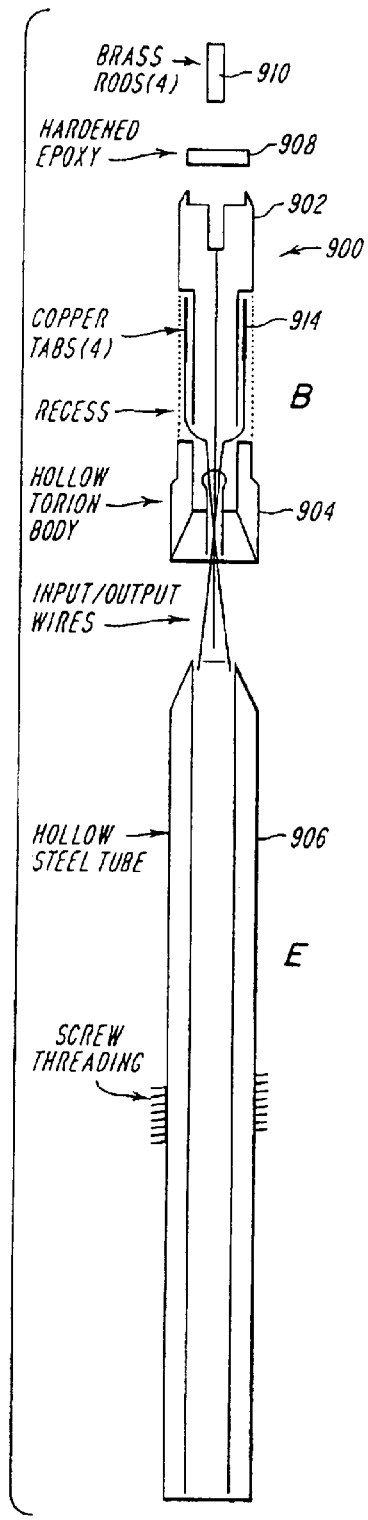

The next step in ETS fabrication involves cutting the ETS into a pattern that enables it to be fit onto the head of the probe. During the photofabrication step, the outlines of the border were also marked onto the ETS. Cutting is performed along the borders with a sharp scalpel. As illustrated in FIG. 8, after cutting, a 0.33 mm thick crucifix shaped plastic backing plate 800 is attached to the piezo side of ETS 802 by a two-part epoxy and dried overnight. Backing plate 802 helps with the alignment of the ETS, described below, and ensures ETS is flat. The present design consisting of the backing plate and the smaller Kynar disk means that the ETS does not have to formed into its final three dimensional shape with a die. The final active area of the ETS is a flat, wrinkle-free surface against the top surface of the core, with no small fold or wrinkle introducing large local stress concentrations that are sensed by the piezo film, significantly distorting the measured signal.

As a final step, a layer of silver chloride is layered onto the silver excitation electrodes. The fully assembled probe is suspended in a bath of unbuffered 0.1 M NaCl, titrated to pH 4.0 with 1 N HCl, and the positive terminal of a variable DC power supply connected to one of the silver electrode wires, in series with an ammeter and a 47 kW resistor. The negative terminal is connected to a platinum strip and suspended in the electrolyte. A current of 120 $\mu$A is run for 10 minutes, corresponding to a total chloride deposition of 1000 (mA-seconds)/cm$^2$, for each electrode of 1.59 mm$^2$ which is acceptable for bioelectric applications.

Probe Structure and Assembly

FIGS. 9a–9d illustrate, collectively, the structure of the probe. Generally, ETS 912 is held in place by pressing it against the inside of a sheath 916 by an inner core 902. This assembly is held inside a shell 918 with a screwed pusher/plunger 906.

The first part of the inner core 902 is preferably a stainless steel head, to accept the stress sensor contacts 910 and is conducting to provide part of the required shielding. Contacts to the stress sensor on ETS 912 are formed by metallic rods 910, preferably brass, at 90° intervals, potted into a recess in the stainless head with a non-conducting two-part epoxy 908. A cruciform pattern is machined in the hardened epoxy 908 to accept a backing plate 800 constructed on ETS 912, illustrated in FIG. 9d. Contacts 910 are electrically isolated from each other and the ground plane (stainless steel head). Prior to potting, each of the 4 contacts 910 are carefully soldered to a wire a cable, which leads to the peripheral circuitry. The cable accommodates four coaxial cables that are especially tailored for low noise applications. The second part of inner core 904 is a plastic body, that provides a means of making the electrical connections to the excitation electrodes, through 4 slots on the periphery that each hold a copper tab 914 connected to a thin wire to carry the driving current.

The insulating (non-conducting) sheath 916 is a thin cylindrical shell made of plastic. Sheath 916 is fitted over ETS 912 that is placed over the end of the inner core 914. The end of sheath 916 is open, exposing the surface of ETS 912 to the cartilage during measurement. Sheath 912 is long enough to cover copper tabs 914 to prevent its contact with stainless steel outer body 918, thus isolating the driving current from ground. In addition, the edge of the sheath is angled to press fit ETS 912 over the rim of the stainless steel head 902 of the inner core 900. The contacts between the silver electrode arms of ETS 912 and copper tabs 914 of inner core 900 are also stabilized by the sheath 916 and sheath 916 provides the pressure to make contact between the electrode arms of ETS 912 and copper tabs 914. A bead of silicon adhesive to seal the probe against the aqueous environment is placed around the periphery of the angled edge before final assembly.

The outer body stainless steel tube 918 is a cylindrical stainless steel tube that acts as a stiff cover to protect the inner components of the probe. One end of outer body 918 is open to expose the surface of ETS 912 but angled to catch the edge on the end of the probe. The other end of outer body 918 is flared outward. Outer body 918 is slid over the sheath/inner core 916. A nut is then slipped over outer body 918, making contact with the threads on pusher/plunger 906, which holds the inner core and non-conducting sheath assembly in outer shell 918. The nut also pulls down upon the flared end of the outer body. As the nut is screwed, outer body 918 is tightened over sheath/inner core 916.

As previously described, the head of the probe has a machined recess 920 in the shape of the crucifix so that ETS 912 fits with the proper orientation to line up the electrical contacts. Brass contacts 910 at the head of the probe receive signals from the piezo electrodes while copper tabs 914 on the side inner core 900 connect with the arms of the silver electrodes. The current is driven through wires leading up to copper tabs 914 and onto the silver electrodes while the current generated stress is transferred to the piezo electrodes and transmitted through brass contacts 910 to the output wires. When assembling the probe, once contacts have been made and pusher/plunger 906 is fitted with inner core 900, sheath 916 is fitted over the head of the probe, making sure ETS 912 is lying flat on the surface of the head. Before sheath 916 is completely fitted over the head, the silver leads are slipped under the copper tabs, and the electrical connections to the silver electrodes are tested. Once all contacts are established, a thin layer of waterproof silicon rubber adhesive is placed on the inside edge of sheath 916. Finally the outer stainless steel cylindrical body 918 is slipped over the probe. Adhesive is also placed on the inside edge of outer body 918 before the probe is finally assembled. Excess adhesive is wiped off the edges. The sealed probe is allowed to dry for at least 24 hours. The active surface of ETS 912 extends slightly beyond the tube end and makes unobstructed contact with the cartilage surface.

Although the present invention has been shown and described with respect to several preferred embodiments thereof, various changes, omissions and additions to the form and detail thereof, may be made therein, without departing from the spirit and scope of the invention.

What is claimed is:

1. A method for detecting degeneration in mammalian cartilage comprising:

applying a current to said cartilage between at least two surface points of said cartilage;

measuring an amplitude of a voltage difference between said at least two surface points resulting from said application of current to said cartilage;

dividing said measured amplitude of said voltage difference by an amplitude of said current to determine an impedance of said cartilage, and comparing said impedance to a normal impedance value of said cartilage previously determined from clinically normal cartilage to detect degeneration of said cartilage.

2. The method for detecting degeneration in mammalian cartilage, as per claim 1, wherein said current is applied into said cartilage at varying depths by changing a spatial distance between said at least two surface points to vary a spatial wavelength of said current.

3. The method for detecting degeneration in mammalian cartilage, as per claim 2, wherein said current is applied to said cartilage via electrodes of an interdigitated electrode array and said spatial distance between said at least two surface points is varied by selectably addressing different electrodes of said interdigitated electrode array to apply said current.

4. The method for detecting degeneration in mammalian cartilage, as per claim 2, wherein said current is applied into said cartilage a short distance from a surface of said cartilage compared to an overall depth of said cartilage to determine an impedance of a superficial region of said cartilage.

5. The method for detecting degeneration in mammalian cartilage, as per claim 2, wherein said current is applied into said cartilage substantially the full depth of said cartilage to determine an average impedance of said cartilage.

6. The method for detecting degeneration in mammalian cartilage, as per claim 1, wherein said measuring step is performed simultaneously with a current generated stress measurement.

7. The method for detecting degeneration in mammalian cartilage, as per claim 6, wherein said current is applied at a frequency in the range of 0.025–1 Hz.

8. The method for detecting degeneration in mammalian cartilage, as per claim 7 wherein said current is sequentially applied at a plurality of frequencies in the range of 0.025–1 Hz and said measuring step is performed at each of said plurality of frequencies.

9. The method for detecting degeneration in mammalian cartilage, as per claim 1, wherein said current is applied at a frequency of about 1 KHz.

\* \* \* \* \*

UNITED STATES PATENT AND TRADEMARK OFFICE
CERTIFICATE OF CORRECTION

PATENT NO. : 6,735,468 B2
DATED : May 11, 2004
INVENTOR(S) : Treppo et al.

It is certified that error appears in the above-identified patent and that said Letters Patent is hereby corrected as shown below:

Column 1,
Line 8, should read
-- This invention was made with government support under Subcontract No. AR 42285, under Prime Grant
No. 2 R44 AR42285 02A1, awarded by the National Institutes of Health. The government has certain rights
in the invention. --

Signed and Sealed this

Thirteenth Day of July, 2004

JON W. DUDAS
*Acting Director of the United States Patent and Trademark Office*